Feb. 26, 1974 L. E. GAVELLO Plant Pat. 3,493
HEBE (VERONICA) PLANT
Filed Oct. 19, 1972
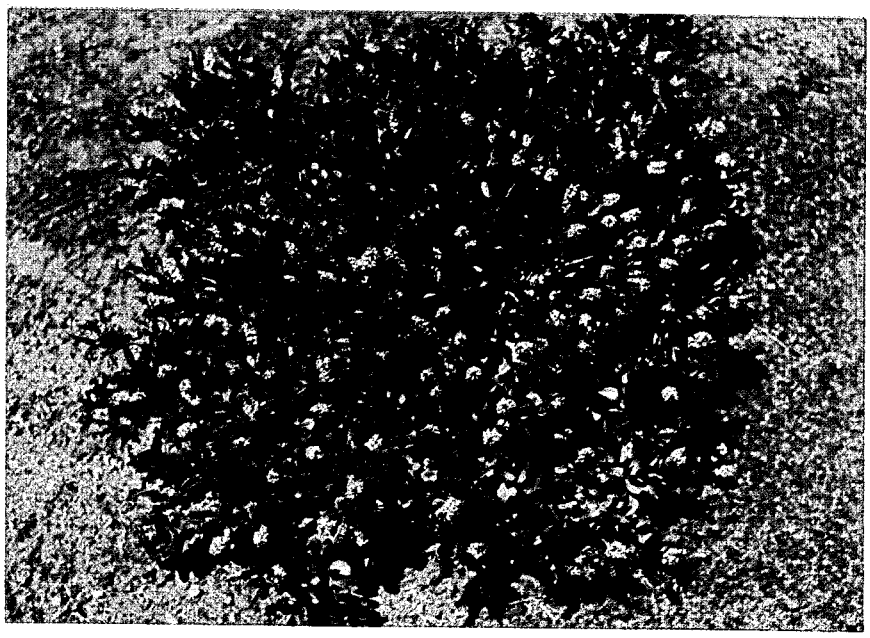
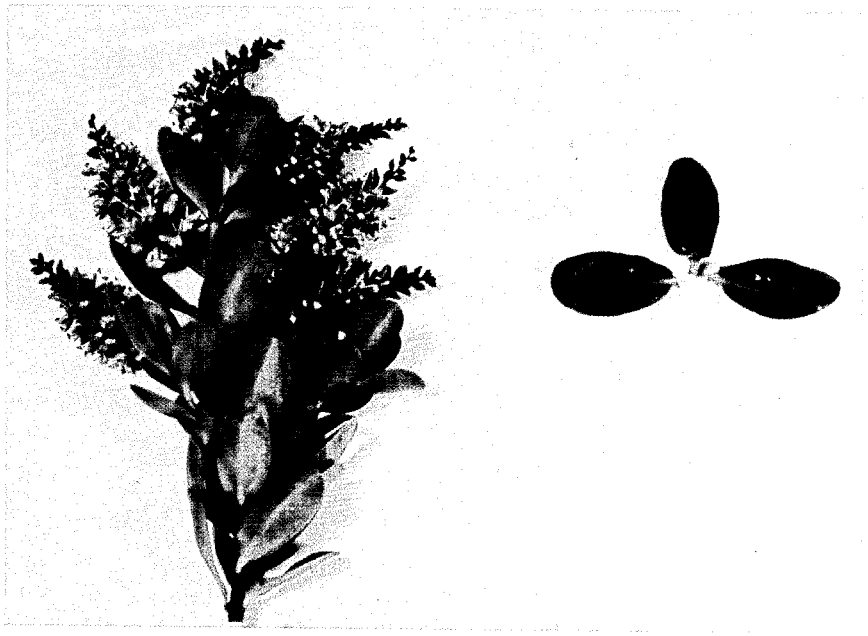

United States Patent Office

Plant Pat. 3,493
Patented Feb. 26, 1974

3,493

HEBE (VERONICA) PLANT

Louis E. Gavello, 3436 Maricopa Ave.,
Richmond, Calif. 94804

Filed Oct. 19, 1972, Ser. No. 298,864
Int. Cl. A01h 5/00
U.S. Cl. Plt.—54 1 Claim My invention relates to a new and distinct variety of Hebe (Veronica) plant discovered in my growing grounds in the summer of 1967 at Richmond, Calif., in a block of about thirty-five, one gallon can size Hebe (Veronica) "Loe," Plant Pat. No. 2,772, and a row of twenty Hebe (Veronica) "Decussata" stock plants.

The plant was first asexually reproduced in April of 1969 by me at my nursery at Richmond, Calif. by cuttings from the original seedling plant. Approximately forty asexual reproductions were then made. The number of generations remain the same.

The parentage is unknown. However, it appears to be a chance seedling from Hebe (Veronica) "Loe" and the Hebe (Veronica) "Decussata" and represents a unique combination which is definitely different from either the Veronica "Loe" or Veronica "Decussata" or in any other variety of Hebe plant of which I am aware.

The accompanying drawing shows, in separate views, a typical plant of my new variety of Hebe plant, a number of racemes on a branch, and specimens of individual leaves, the same being depicted in color as nearly true as it is reasonably possible to make the same in a color illustration of this character.

Among the outstanding characteristics of the new variety, the following features contribute to the novelty and distinctiveness thereof:

FORM

The plant is of the prostrate, trailing ground cover type, growing to a height of only about 16 inches and is procumbent.

FOLIAGE

The leaves are evergreen, glabrous elliptical to obovate, sub-coriaceous, and of a length from ⅞ to 1½ inches long and from ½ to ⅞ inches wide. In color, the leaves are firgreen in accordance with plate 24–8–L on pages 70–71 by Maerz and Paul, Dictionary of Color, 2nd Edit., 1950.

The leaves are arranged opposite in pairs, decussate, and are spaced ¼ to ⅞ inches apart.

Each leaf has one prominent mid-rib from base to tip, with a margin which is entire and smooth.

FLOWERS

Blooms start in the area of Richmond, Calif., approximately the middle of April and continue until about the end of July, and repeat around October and continue until frost.

Racemes run 6 to 8 in upper axils; elongate conical; 2½ to 3½ inches long. Width at base of flower, ¾ to 1 inch.

Florets are Campanula blue as compared with Plate 42 10–J on pages 106–107 of Dictionary of Color, 1950 by Maerz and Paul, on short pedicels, each subtended by a small bract. There are about forty to fifty per raceme. Corollas are four lobed, the dorsol broader than the ventral; with laterals about equal. As to size, the corollas are about ⅜ inches long and about ⅜ inches long and about ⅜ inches across. Stamens are two in number, with anthers small on exserted subulate filaments.

GROWTH

The plant grows best in the sun, in the San Francisco Bay area. Inland, it should do better planted in area where it will get the morning sun.

DISEASE RESISTANCE

As to disease resistance, this plant is free of major diseases.

Having described and illustrated my new variety of Hebe (Veronica) plant, I claim:

1. A new and distinct variety of Hebe (Veronica) plant substantially as illustrated and described and characterized as to novelty by
   (a) Low growing, trailing ground cover type plant
   (b) Profuse flowers of color "Campula Blue" covering the entire plant
   (c) Its long and repeated blooming period, and
   (d) Its resistance to weather and diseases.

No references cited.

ROBERT E. BAGWILL, Primary Examiner